US00PP20183P3

(12) United States Plant Patent
Stever

(10) Patent No.: US PP20,183 P3
(45) Date of Patent: Jul. 28, 2009

(54) ***MAHONIA* PLANT NAMED 'SOFT CARESS'**

(50) Latin Name: ***Mahonia* sp.**
Varietal Denomination: Soft Caress

(75) Inventor: Karen Reiter Stever, Gainesville, GA (US)

(73) Assignee: ItSaul Plants, LLC, Atlanta, GA (US)

( * ) Notice: Subject to any disclaimer, the term of this patent is extended or adjusted under 35 U.S.C. 154(b) by 266 days.

(21) Appl. No.: 11/325,030

(22) Filed: Jan. 4, 2006

(65) Prior Publication Data

US 2007/0157352 P1 Jul. 5, 2007

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
*Assistant Examiner*—Georgia Helmer
(74) *Attorney, Agent, or Firm*—Penny J. Aguirre

(57) ABSTRACT

A new cultivar of hybrid *Mahonia,* 'Soft Caress', characterized by its unique foliage comprises of leaves with narrow, thread-like leaflets combined with a vigorous growth habit, racemes of yellow flowers, and pruinose blue berries.

3 Drawing Sheets

Botanical classification: *Mahonia* sp.
Variety denomination: 'Soft Caress'.

BACKGROUND OF THE INVENTION

The present invention relates to a new and distinct cultivar of *Mahonia* sp. as the specific epithet could not be determined. The new cultivar will be referred to hereafter by its cultivar name, 'Soft Caress'. 'Soft Caress' is an evergreen shrub grown for use as a landscape plant.

The inventor discovered 'Soft Caress' as a naturally occurring whole plant mutation in summer of 2001 in a nursery in Chamblee, Ga. The new cultivar was derived from sown seeds of unnamed plants of *Mahonia* sp. 'Soft Caress' was selected primarily for its unique thread-like foliage, a characteristic that is not known to exist in species and cultivars of *Mahonia* known to the inventor.

Asexual reproduction of the new cultivar was first accomplished by the inventor using softwood stem cuttings in summer of 2002 in Chamblee, Ga. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial garden for three years in Atlanta, Ga. These attributes in combination distinguish 'Soft Caress' as a unique cultivar of *Mahonia.*

1. 'Soft Caress' has foliage with threadlike leaflets, much narrower than the foliage of all species and cultivars of *Mahonia* known to the inventor.
2. 'Soft Caress' is an evergreen shrub suitable for growing in shady and partially sunny conditions.
3. 'Soft Caress' exhibits racemes of yellow flowers from mid November to mid January with occasional re-bloom through out the growing season in Georgia with subsequent development of pruinose blue berries.
4. 'Soft Caress' exhibits a vigorous growth habit.

BRIEF DESCRIPTION OF THE DRAWING

The accompanying colored photographs illustrate the overall appearance and distinct characteristics of the new *Mahonia* as grown in Atlanta, Ga.

The photograph in FIG. 1 was taken in October and illustrates the plant habit of 'Soft Caress' as grown outdoors for three years in a three-gallon container in partial shade in Atlanta, Ga.

Figure 1:
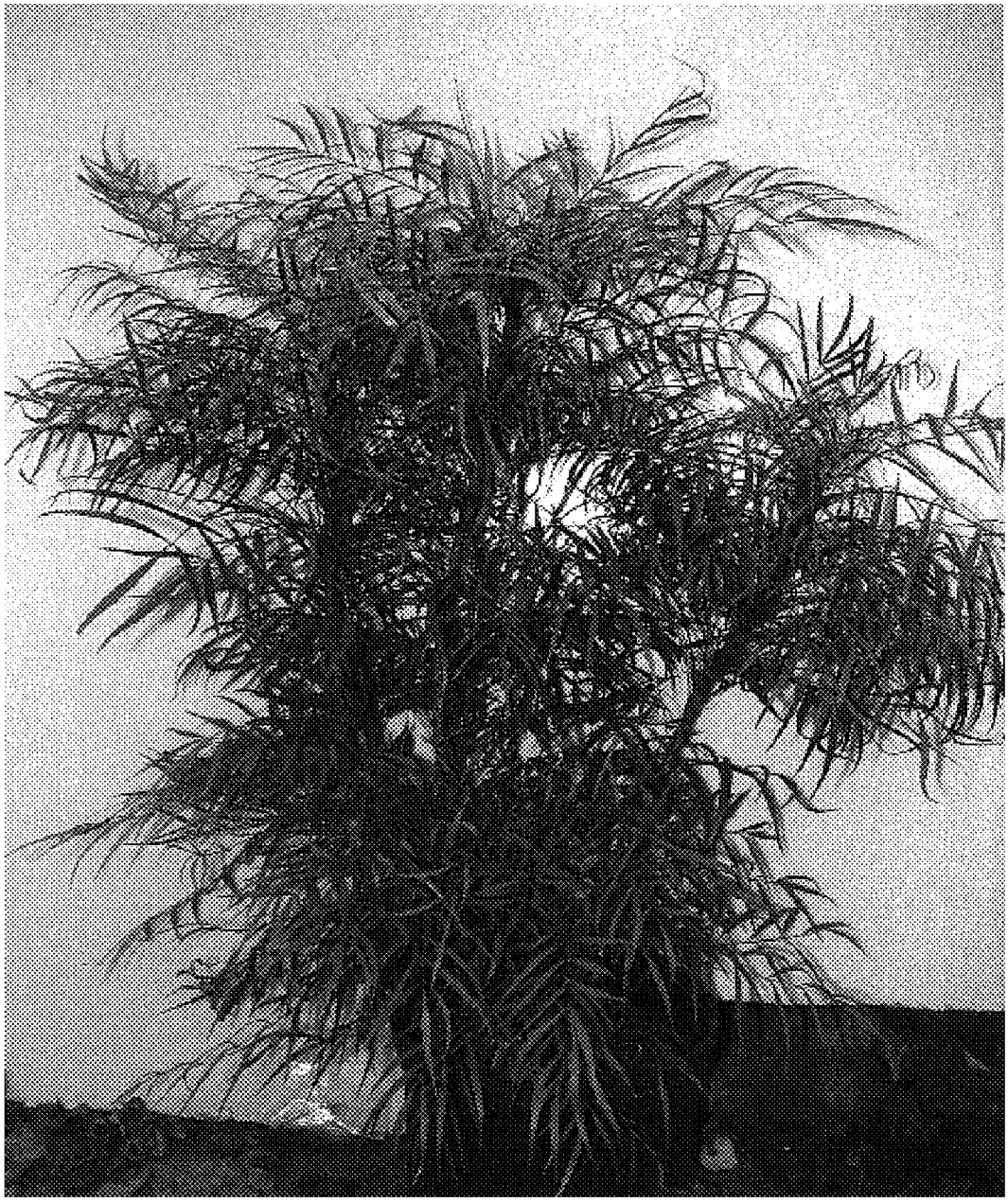
Figure 2:
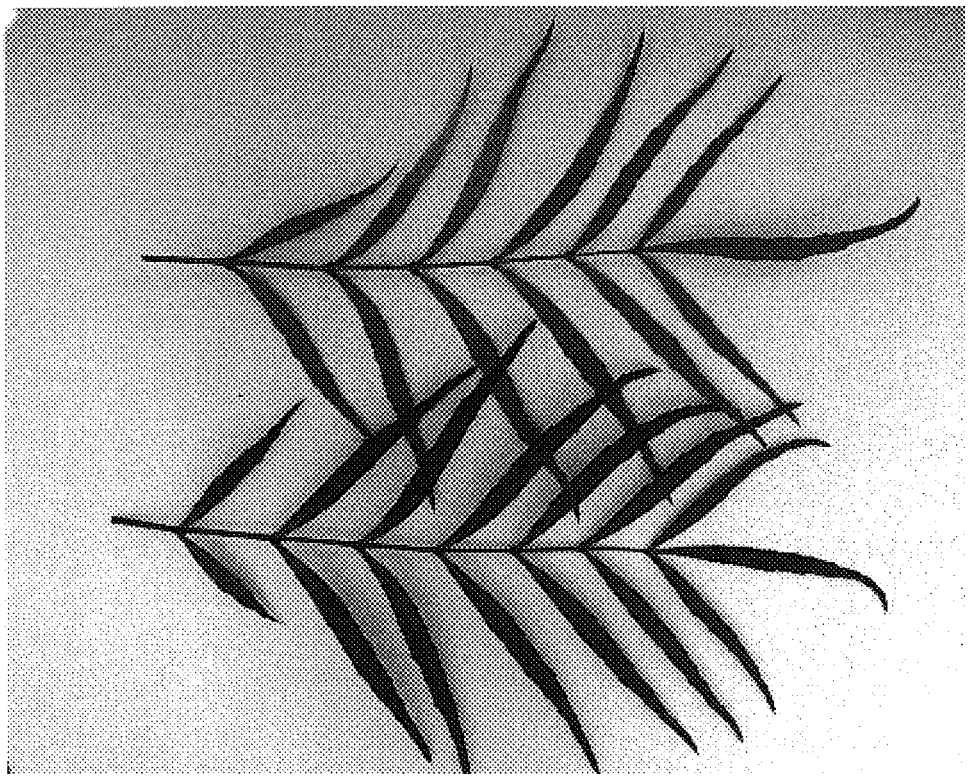
Figure 3:
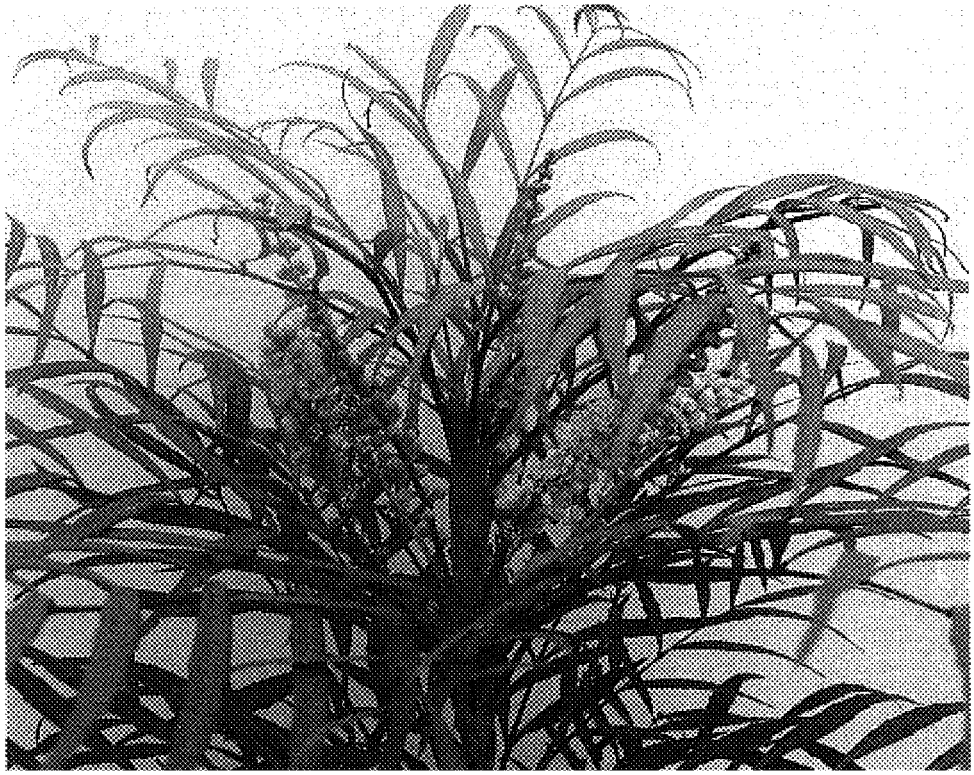
Figure 4:
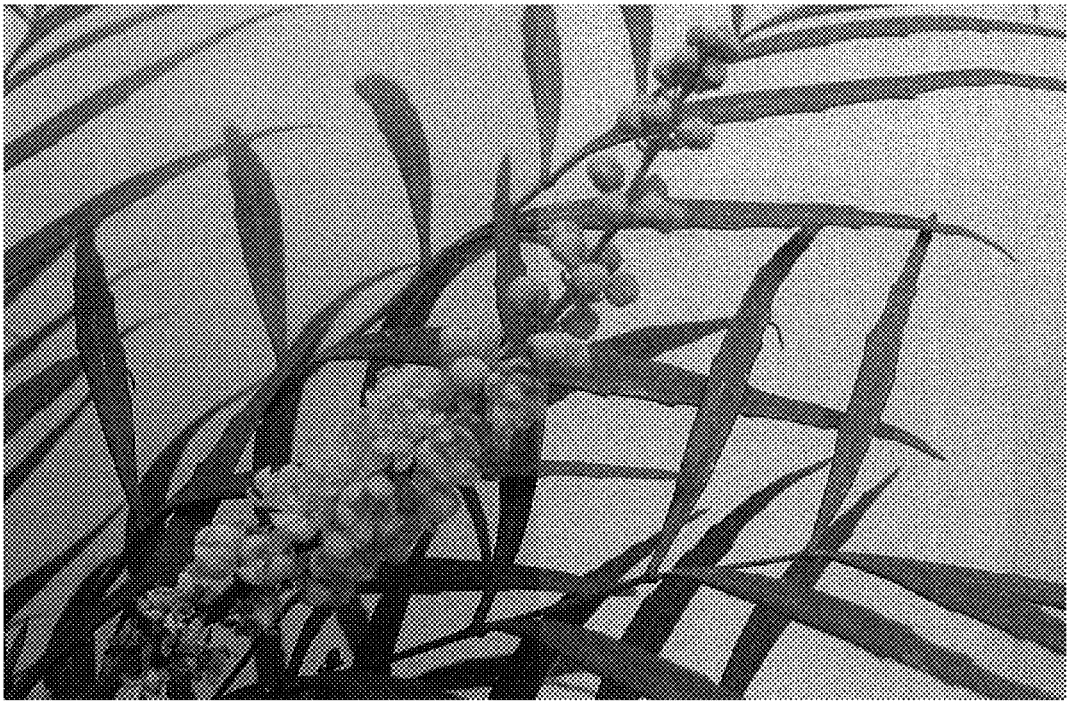

The photographs in FIG. 2, FIG. 3 and FIG. 4 were taken in February of a one year-old plant of 'Soft Caress' as grown in a one-gallon container outdoors in Atlanta, Ga.

FIG. 2 provides a close-up view of the foliage with the lower surface of the leaf depicted on the top and the upper surface of the leaf depicted on the bottom, FIG. 3 is a side view of the plant in bloom and FIG. 4 provides a close-up view of a raceme of flowers.

Figure 5:
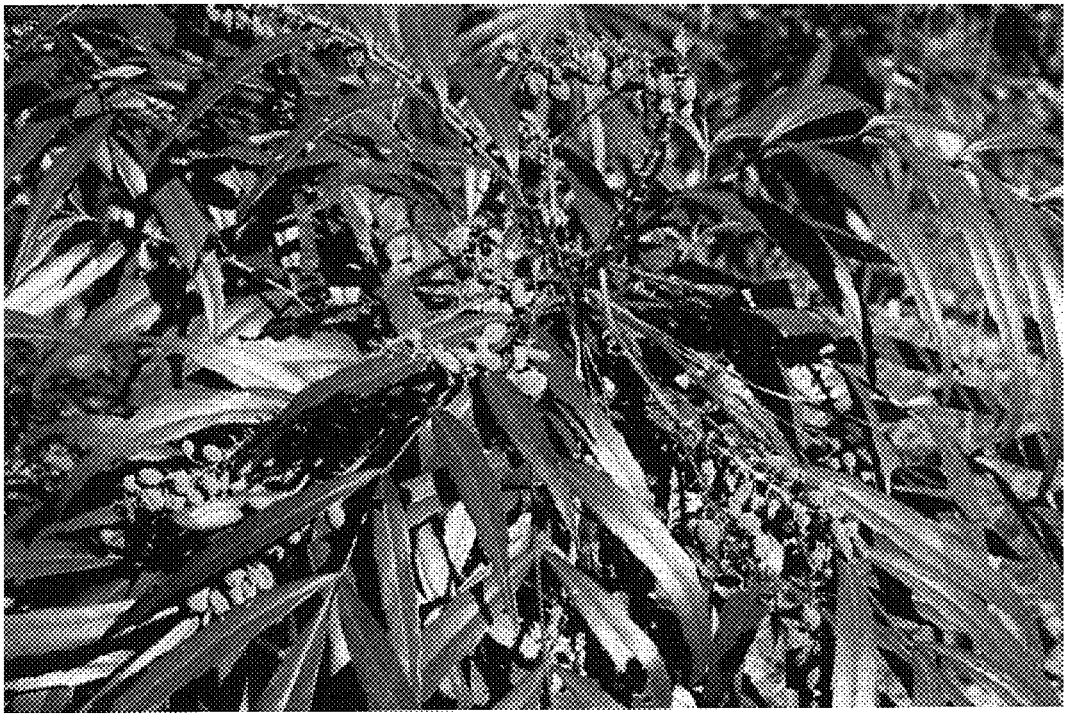

The photograph in FIG. 5 was taken in early winter and provides a view of the fruit on a 3 year-old plant of 'Soft Caress'.

The colors in the photographs are as close as possible with the digital photography techniques available, the color values cited in the detailed botanical description accurately describe the colors of the new *Mahonia.*

DETAILED BOTANICAL DESCRIPTION

The following is a detailed description of the new cultivar as grown outdoors in partial shade in a trial garden in Atlanta, Ga. for three years. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Botanical classification.*—*Mahonia* 'Soft Caress', a cultivar of *Mahonia* sp.

*Parentage.*—Naturally occurring whole plant mutation of unnamed plants of *Mahonia* sp.

*Blooming period.*—Blooms for approximately 4 weeks, typically from mid January to mid February in Georgia.

*Plant habit.*—Evergreen shrub, open habit.

*Height and spread.*—Reaches about 1 m in height and about 0.8 m in width after three years of growth.

*Cold hardiness.*—U.S.D.A. Zone 6.

*Diseases and pests.*—No susceptibility or resistance to diseases or pests known to affect *Mahonia* has been observed for 'Soft Caress'.

*Root description.*—Fleshy.

Growth and propagation:

*Propagation.*—Terminal, softwood stem cuttings.

*Root initiation.*—Roots develop in 4 weeks in summer under greenhouse conditions under intermittent mist without supplemental lighting.

*Time required for root development.*—3 weeks to develop a 72 cell plug from a rooted cutting under greenhouse conditions under ambient light.

*Growth rate.*—Vigorous.

Stem description:

*Shape.*—Round, robust, knotty due to sheathing of petioles.

*Stem color.*—New growth emerges N144A, maturing to 144A.

*Stem size.*—Main stems; about 1 m in length and 2.5 cm in diameter, lateral branches; about 50 cm in length and 4 mm in width.

*Stem surface.*—Glabrous.

*Internode length.*—Average of 1.5 to 2 cm.

*Branching.*—Basal branches are predominant with an average of 1 to 3 lateral branches.

Foliage description:

*Leaf shape.*—Oval to ovate.

*Leaf division.*—Imparipinnate (odd-pinnate).

*Leaf base.*—Attenuate (leaf and leaflets).

*Leaf apex.*—Acute (leaf and leaflets).

*Leaf fragrance.*—None.

*Leaflet venation.*—Not prominent, midrib is conspicuous on lower surface only, 138A in color.

*Leaflet margins.*—Spiny-serrate with 4 to 6 serrations per side.

*Leaf arrangement.*—Whorls, leaflets are opposite.

*Leaf attachment.*—Petiolate, leaflets sessile.

*Leaf surface.*—Glabrous to slightly lustrous on upper surface, glabrous to slightly glaucous on lower surface.

*Leaf size.*—Average of 18 cm in length and 10 cm in width.

*Leaflet size.*—Range from about 3 to 8.5 cm in length and 4 to 8 mm in width.

*Leaflet internode length.*—0.5 to 2.5 cm (average of 1.25 cm).

*Leaf quantity.*—Average of 12 leafs per whorl and 11 to 15 leaflets per leaf.

*Leaf color.*—Newly expanded leaves; upper surface 144A, lower surface, mature leaves; upper surface 139A, lower surface color between 138A and 138B.

*Petioles.*—About 1 cm in length, 5 mm in width, sheathed around stem at ligule, 146B in color.

*Rachis.*—Round, about 11 to 15 cm in length, 1 to 2 mm in diameter, surface is slightly lustrous, color on young and mature leaves is 144A overlaid with 200 on upper surface and 144A on lower surface.

*Ligules.*—Membranous, 1 mm in width, 146B in color.

*Stipules.*—Present above leaf whorls (reduced stipule-like leaves), about 2 cm in length and 5 mm in width tapering to a point, 144A to 144B in color turning to 200C.

Inflorescence description:

*Inflorescence type.*—Fascicles of racemes arranged in whorls emerging above leaf whorls, racemes open from bottom of raceme towards apex, racemes of tightly packed cup-shaped flowers.

*Flower buds.*—Conical in shape with acute apex, up to 1.5 cm in length and 1 cm in width prior to opening, calyx portion is wrapped around petals and 145C in color, petal portion emerges N144B in color and changes to 9A prior to opening.

*Flower fragrance.*—Sweet-scented.

*Lastingness of inflorescence.*—About 10 days from the opening of the lower flowers to the opening of the upper flowers of the raceme, not persistent.

*Flower quantity.*—About 50 flowers per raceme, 5 to 8 racemes per whorl, new whorls arise about new growth of foliage for duration of flowering season.

*Flower type.*—Perfect, cup-shaped.

*Flower aspect.*—Outward facing on raceme, racemes are held at about a 30 to 40° angle from the stem.

*Flower size.*—Average of 8 mm in diameter and 4 cm in depth.

*Raceme size.*—Up to 14 cm (from base of peduncle) and about 2.5 cm in diameter.

*Peduncles.*—Up to 14 cm in length and 2 mm in diameter, N144A in color.

*Pedicels.*—About 2 mm in length and 0.5 mm in diameter, 144B in color.

*Flower buds.*—Globose in shape, up to 4 mm in diameter, N144C in color changing to 151C prior to opening.

*Petals.*—6, arranged in 2 whorls of 3, un-fused, obovate to oblong in shape, upper and lower surface is glabrous, entire margin, square base, retuse apex, about 3 cm in length and 1.5 to 2 mm in width, color is 1A when opening (lower and upper surface) maturing to 3A (lower and upper surface), curved inward.

*Calyx.*—Composed of 2 whorls of 3 petaloid sepals.

*Sepals.*—6, obovate in shape, 3A in color, glabrous surface, about 4 to 5 mm in length and 3 mm in width, entire margin, round apex and attenuate base.

Reproductive organs:

*Gynoecium.*—1 pistil, about 2 mm in length and 1 mm in width, style is very short and stout and 144C, single peltate stigma is 144C in color, ovary is superior, 1-celled and 144C in color.

*Androecium.*—6 stamens, un-fused but curved next to inner surface of petals, filaments are 145C in color, about 9 mm in length and 0.3 mm, anthers are 145C in color and open by 2 valves, pollen was moderately abundant, 145C but glistening or crystal-like in appearance.

*Fruit and seed.*—Berry, ovoid in shape, about 7 mm in length and 3.5 mm in width, pruinose surface, 98C to 98D in color, mature seeds were not observed under the conditions tested.

I claim:

1. A new and distinct cultivar of *Mahonia* plant named 'Soft Caress' as herein illustrated and described.

* * * * *